United States Patent
Circo et al.

(10) Patent No.: US 12,004,851 B1
(45) Date of Patent: Jun. 11, 2024

(54) METHODS FOR AUTOMATIC COUGH DETECTION AND USES THEREOF

(71) Applicants: Iulian-Alexandru Circo, Vienna (AT); Joseph Russell Brew, Santa Coloma de Queralt (ES); Paul Simon Rieger, Vienna (AT); Peter McMichael Small, Seattle, WA (US); Georgios Kafentzis, Heraklion Crete (GR)

(72) Inventors: Iulian-Alexandru Circo, Vienna (AT); Joseph Russell Brew, Santa Coloma de Queralt (ES); Paul Simon Rieger, Vienna (AT); Peter McMichael Small, Seattle, WA (US); Georgios Kafentzis, Heraklion Crete (GR)

(73) Assignee: HYFE Inc., Wilmington, DE (US)

( * ) Notice: Subject to any disclaimer, the term of this patent is extended or adjusted under 35 U.S.C. 154(b) by 0 days.

(21) Appl. No.: 18/429,130

(22) Filed: Jan. 31, 2024

Related U.S. Application Data (60) Provisional application No. 63/442,310, filed on Jan. 31, 2023.

(51) Int. Cl.
*A61B 5/08* (2006.01)
*A61B 5/00* (2006.01)

(52) U.S. Cl.
CPC .......... *A61B 5/0823* (2013.01); *A61B 5/7267* (2013.01)

(58) Field of Classification Search
CPC .............................. A61B 5/0823; A61B 5/7267
See application file for complete search history.

(56) References Cited

U.S. PATENT DOCUMENTS

2022/0338756 A1* 10/2022 Dzhekiev ................ G10L 25/66
2023/0008906 A1*  1/2023 Taylor ................... A61B 5/0823

FOREIGN PATENT DOCUMENTS

WO   WO-2023044541 A1 *  3/2023
WO   WO-2023239327 A1 * 12/2023

\* cited by examiner

*Primary Examiner* — Tammie K Marlen
(74) *Attorney, Agent, or Firm* — Boris Leschinsky (57) ABSTRACT

A method of automatically detecting cough events from a continuous recording of ambient sound includes a step of detecting an onset of a possible cough event by analyzing acoustic energy distribution of an audio snippet in a frequency-time domain at a frequency above 100 Hz and classifying the event as a cough or a non-cough using convolutional neural networks. The method may be used for improved diagnosis in differentiating between various diseases having cough as a common symptom, monitoring the progression of a disease or efficacy of a treatment and for other purposes.

17 Claims, 5 Drawing Sheets

METHODS FOR AUTOMATIC COUGH DETECTION AND USES THEREOF

CROSS-REFERENCE DATA

This patent application claims a priority date benefit from a U.S. Provisional Patent Application No. 63/442,310 filed on 31 Jan. 2023 and entitled "Digital methods for cough detection and drug-free treatment," the content of which is incorporated herein in by reference.

BACKGROUND

Without limiting the scope of the invention, its background is described in connection with recognizing and recording cough events using ambient sound recording. More particularly, the invention describes methods for automatic detection of cough and separating cough and non-cough events.

Cough, being one of the most common symptoms of a wide range of respiratory conditions—from common colds to more serious ailments like COVID-19, tuberculosis, and asthma—serves as a vital indicator of health status. However, manual monitoring of cough frequency and patterns is labor-intensive, subjective, and prone to error, especially in crowded environments like hospitals, nursing homes, or public spaces.

Automated cough detection using ambient sound recording addresses a crucial need in healthcare and public health monitoring. Implementing an automated cough detection system can vastly improve the accuracy and efficiency of this monitoring. By continuously analyzing ambient sounds, these systems can identify cough sounds, differentiating them from other environmental noises. This capability is particularly useful in managing and controlling the spread of infectious diseases. For instance, in a post-COVID-19 world, early detection of coughing in a public space can prompt quicker response measures, reducing the risk of viral transmission.

Moreover, in a clinical setting, automated cough monitoring can provide healthcare professionals with valuable data about a patient's condition without the need for constant human observation. This system can track changes in cough frequency and character, aiding in the assessment of disease progression or recovery. It's also beneficial for patients with chronic respiratory conditions, allowing for remote monitoring and timely interventions based on cough analysis.

In addition, such technology can significantly contribute to large-scale epidemiological studies and public health surveillance. By analyzing cough patterns from a wide population, health authorities can gain insights into the prevalence and spread of respiratory diseases, enabling better-informed public health decisions and strategies.

Lastly, automated cough detection using ambient sound recording is minimally invasive and respects privacy, as it doesn't require direct interaction with the individuals being monitored. This feature makes it a viable option for continuous monitoring in various settings, from individual homes to public areas, without raising significant privacy concerns.

Modern automated systems for cough detection and monitoring, despite their advancements and utility, face several significant limitations and drawbacks. One of the primary challenges is maintaining accuracy in detecting coughs. These systems often struggle to distinguish cough sounds from other similar noises, leading to false positives (erroneously identifying non-cough sounds as coughs) and false negatives (failing to recognize actual coughs). The variability in how coughs sound, influenced by individual differences, the specific illness causing the cough, and environmental factors, adds complexity to accurate cough detection.

Another major concern is privacy. Continuous ambient sound recording for cough detection inevitably raises questions about user privacy and data security. Even if the systems are designed solely to identify coughs, the fact that they are constantly listening can be a source of anxiety for individuals, especially in private settings. Ensuring the security of collected data and compliance with privacy laws like the Health Insurance Portability and Accountability Act (HIPAA) in the United States is a critical challenge.

Furthermore, these systems can generate vast amounts of data, leading to potential issues with data overload and management. The need for secure storage, efficient processing, and accurate analysis of this data can be resource-intensive, posing a significant challenge, particularly in large-scale deployments. The performance of cough detection systems is also influenced by the ambient environment. Factors such as background noise, room acoustics, and the distance between the sound source and the recording device can impact the accuracy of detection.

The cost of developing, implementing, and maintaining these sophisticated systems can be substantial, limiting their accessibility, especially in under-resourced settings where such technology could be highly beneficial. Additionally, there are ethical and social implications to consider. The potential for these systems to be used for purposes beyond health monitoring, such as surveillance, is a concern. Societal acceptance of continuous monitoring technologies varies across different cultures and settings, and this disparity can affect the widespread adoption of these systems.

Integration of these systems into existing healthcare frameworks poses its own set of challenges. Healthcare professionals may require additional training to interpret and utilize the data effectively. This integration process needs to be seamless and intuitive to ensure that the data collected can be translated into actionable medical insights.

Moreover, these systems are dependent on consistent technological infrastructure and power supply, which might not be readily available in remote or underdeveloped areas. This dependency limits the reach of such technology to regions that can support it. Lastly, while automated cough detection systems can provide valuable data on cough frequency and patterns, the interpretation of this data in a clinical context is not straightforward. Cough is a non-specific symptom common to many conditions, and deciphering the underlying cause or severity based solely on cough patterns requires careful clinical judgment and additional contextual information.

The need exists, therefore, for an improved methodology of automated cough detection, which addresses the above-mentioned limitations of other known systems.

SUMMARY

Accordingly, it is an object of the present invention to overcome these and other drawbacks of the prior art by providing novel methods for automated cough detection with improved accuracy and reliability.

It is another object of the present invention to provide novel methods for automated cough detection with efficient data processing that may be implemented on a smartphone or another small electronic device.

It is a further object of the present invention to provide novel methods for automated cough detection that address privacy concerns and provide objective cough recording without recording other data that may compromise user privacy.

The method of automatically detecting cough events of the present invention may include the following steps:
a. continuously recording ambient sound,
b. upon detecting a change in ambient sound exceeding a predefined first threshold, identifying an onset of a possible cough event,
c. recording an audio snippet including the onset of a possible cough event and continuing for a predefined audio snippet duration exceeding 100 msec thereafter,
d. classifying the audio snippet recorded in step (c) as cough or non-cough based on analyzing acoustic energy distribution of the audio snippet in a frequency-time domain at a frequency above 100 Hz,
e. discarding all identified non-cough events,
f. repeating steps (b) through (e) if further possible cough events are identified after the audio snippet recorded in step (c), and
g. compiling a record of all cough events detected during the duration of continuously recording ambient sound in step (a).

Recording ambient sound may be done using a microphone connected to the computerized control unit configured to implement the method of the present invention. This computerized control unit may be a smartphone. The method of the invention may be a software program or application running on a smartphone, tablet, or another small electronic device capable of processing data detected by a microphone attached thereto or incorporated therewith.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The method of automatically detecting cough events may include a step of continuously recording ambient sound. This may be done using a suitable microphone or another sound-detecting device having sufficient sensitivity to produce an audio signal that may be processed for cough detection purposes. Microphones incorporated in most modern smartphones, tablets, smartwatches, and laptop computers are some examples of suitable microphones for the purposes of the present invention.

A computerized control unit configured to implement the method of the present invention may be used for collecting and processing the audio signal recorded using a microphone connected thereto. Such control unit may be that of a smartphone, or another small electronic device. It may also be a part of a larger system such as a hospital-grade patient monitoring system, or an observation system configured to monitor a larger number of people gathered together in one place, as the invention is not limited in this regard.

The sound signal feed may be continuously analyzed in real time or after the recording is produced. Various parameters of the sound signal may be monitored, such as amplitude, frequency distribution, sound pressure, etc. Broadly speaking, the present invention uses acoustic energy to detect cough events and differentiate cough events from non-cough events.

Acoustic energy broadly refers to the energy carried by sound waves. Sound waves are a type of mechanical wave, meaning they require a medium (like air, water, or solid materials) to travel through. These waves are created by the vibration of an object, which causes the air particles around it to vibrate as well. This vibration of air particles (or particles in other mediums) transmits energy from one place to another, which we perceive as sound.

The detailed nature of acoustic energy can be understood through its calculation and monitoring. Acoustic energy is typically characterized in terms of its intensity and/or sound pressure. Intensity may be understood as the power carried by sound waves per unit area in a direction perpendicular to that area. Sound pressure, in turn, can be measured using a microphone, which converts the pressure variations caused by sound waves into electrical signals. Acoustic energy may also be characterized by its frequency, which determines the pitch of the sound, and its amplitude, which determines the loudness. Monitoring acoustic energy thus involves not only measuring its intensity and pressure but also analyzing these other characteristics.

The process of human coughing, a complex and common reflex that helps protect the respiratory system, can be broken down into several distinct phases, each characterized by specific physiological actions and associated sounds.

1. Inspiratory Phase: The cough reflex begins with the inspiratory phase, where there is a deep inhalation. During this phase, air is rapidly drawn into the lungs, leading to the expansion of the chest and lungs. The sound associated with this phase is typically a sharp intake of breath, which may not be very loud but is an essential precursor to the subsequent phases of the cough.
2. Compression Phase: Following the inspiratory phase, the glottis (the opening between the vocal cords) closes, and the muscles of the chest and abdomen contract forcefully. This action increases the pressure within the lungs significantly. There is no distinct sound produced during this phase as the airway is temporarily closed. However, this phase is critical in building up the pressure needed to create an effective cough.
3. Expulsive Phase: This is the phase where the actual cough occurs. It starts with the sudden opening of the glottis, releasing the pressurized air in the lungs. This rapid expulsion of air helps to dislodge and remove any irritants or secretions from the respiratory tract. The sound produced during this phase is the characteristic "cough" that we are familiar with. It can vary in intensity and tone based on factors such as the volume of air expelled, the size of the airways, and the nature of the cough (dry or productive).
4. Post-tussive Respiration: Though not always considered a separate phase, this involves the recovery breaths taken after the cough. Depending on the intensity and duration of the cough, these breaths can be deep and labored or quick and shallow. There might be a wheezing or gasping sound if the airways are narrowed or obstructed.

Each of these phases contributes to the effectiveness of the cough as a mechanism for clearing the airways. The third and fourth phases of the cough reflex may generally be manifested as a cough sound. Cough sounds may share common attributes such as a relatively loud intensity, quick burst of sounds, and predictable duration and falloff. The overall energy of a cough reflex may be much stronger relative to the surrounding environment, and the initial burst of air may cause a significant acoustic energy change as compared to ambient noise and regular ambient sounds. The present invention is generally directed to detect cough events using the third, expulsive phase sounds and identifying the number of events when a third phase of the cough is detected over a desired period of time.

Surrounding sound or ambient sound may be recorded continuously or over a specified period of time. To reduce computational demand, a simple monitoring of sound amplitude or loudness may be conducted on a continuous basis. Once the amplitude exceeds a predefined first threshold, indicating an onset of a louder sound above the regular ambient sound, which may be associated with a possible sough event, the method of the invention described below may be implemented to discern whether the onset of the louder sound was a cough event or not. In other embodiments, monitoring other ambient sound parameters may be used to identify a change in ambient sound which is sufficient to implement further steps of the method of the invention. Examples of other parameters characterizing the ambient sound may include acoustic energy, intensity, sound pressure, and frequency distribution. The level of the first predetermined threshold may be selected depending on the current level of ambient noise. The lower the noise, the lower may be the value of the first threshold. If the ambient background noise is significant, the first threshold may be increased to limit the number of false positive readings indicating the onset of a possible cough event.

In further embodiments, a step of continuously recording ambient sound may further include a step of removing some portions of the audio recording identified as silence sounds. Silence sounds may be identified using a predefined silence threshold.

In further embodiments, the monitoring and/or recording of the ambient sound may be conducted within a certain range of frequencies that correspond to a frequency range characterizing a human cough. More specifically, the range of frequencies that are of interest to detect a possible cough event may start at about 100 Hz as sounds below that frequency are unlikely to be associated with a human cough. In embodiments, the upper limit of the frequency interest range may be selected to be 8,000 Hz. The upper limit of the frequency range may be reduced below about 8,000 Hz to limit the computing power demand, as frequencies higher than 8000 Hz are not typically associated with significant changes in the acoustic energy of the cough onset. In further embodiments, the lower limit and the upper limit of the frequency range may be selected based on the quality of the recorded audio snippet. For example, for an audio snippet recorded at 16,000 Hz, the range of frequency that is of interest for the purposes of the present invention may be selected to be from about 100 Hz to about 7,500 Hz. In another example, this range may be reduced to a range from about 100 Hz to about 3900 Hz for an audio snippet recorded at 8,000 Hz.

Following the analysis and classification outcome of the audio recording, the non-cough events may be discarded, while each cough event may be recorded with a time stamp corresponding to the onset thereof. A record of cough events may be produced and used for further processing. Such records may include none of the time stamps associated with cough events, at least one time stamp for one cough event, at least two time stamps, and so on. After the possible cough event is analyzed and classified into a cough or a non-cough status, the system may return to monitoring for further onsets of possible cough events and process each onset as described below.

Once a change in ambient sound above the predetermined first threshold is detected, the method of the invention teaches to record an audio snippet of the possible cough event, which includes the onset that triggered the creation of the audio snippet. The audio snippet may be of a predetermined duration from the onset, such as at least 100 msec, at least 150 msec, at least 200 msec, at least 250 msec, at least 300 msec, at least 350 msec, at least 400 msec, at least 450 msec, or at least 500 msec from the onset. The audio snippet may not exceed about 1 sec in duration from the onset of the possible cough event.

In other embodiments, the starting point of the audio snippet may be selected to be earlier than the onset of the possible cough event, such as at least 20 msec earlier or more. The segment of the audio snippet recorded prior to the onset of the possible cough event may be used to measure the ambient sound just before the onset of the possible cough event for the purpose of comparing it with the sound characterizing the possible cough event, as discussed below in greater detail.

Once the audio snippet is created, it may undergo further analysis and classification as a cough event or a non-cough event. Non-cough events are discarded, while individual cough events are assigned individual time stamps corresponding to a respective onset of each cough event.

Figure 1:
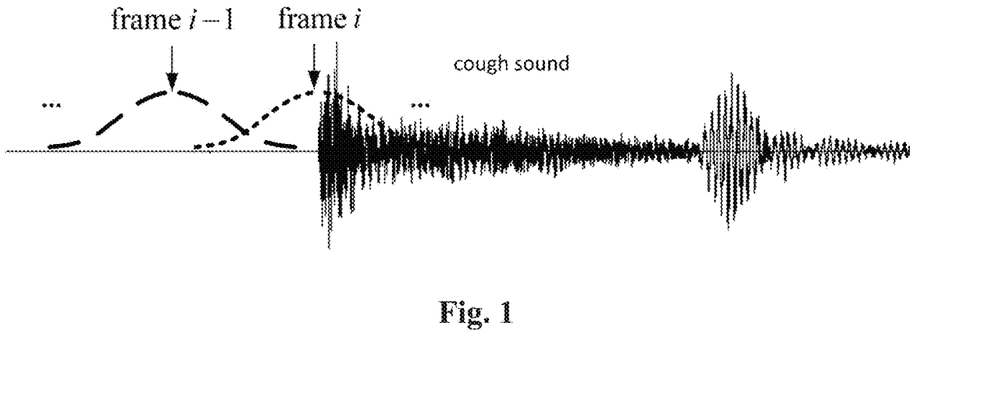
FIG. 1 is one example of recorded ambient sound, including a cough event.

FIG. 1 shows an example of an audio snippet recording containing a possible cough event. Analysis of the audio snippet to confirm the true onset of a possible cough event may be done by identifying the acoustic energy distribution thereof in a frequency-time domain. More specifically, this may be done by detecting individual changes in acoustic energy in a plurality of bins, wherein each bin corresponds to a predefined acoustic frequency or a narrow range of acoustic frequencies.

The audio snippet may first be divided into a plurality of time frames, such as at least 2 or more time frames. The duration of each time frame may be from about 15 to about 50 msec. Time frames of the plurality of time frames may overlap, such as by at least 1% of the total time frame duration, by at least 5% of the total time frame duration, by at least 10% of the total time frame duration, by at least 20% of the total time frame duration, by at least 30% of the total time frame duration, by at least 40% of the total time frame duration, or up to about 50% of the total time frame duration. In other embodiments, the overlap between successive time frames may vary from as little as a single sample in discrete time, which equals the inverse of the sampling rate. The overlap may be as high as the entire duration of a single time frame, which, as described above, can vary from about 15 msec to about 50 msec.

In one example, the duration of each time frame may be set at 48 msec, with each successive frame shifted to the right of the previous frame by 32 msec, therefore defining an overlap between two successive frames at 16 msec. in this example, a 60-second record of the ambient sound may be divided into about (60-0.048)/0.032=1873 overlapping time frames.

In further embodiments, the duration of the time frame and/or the overlap between two adjacent time frames may be variable and adaptive depending on the spectral and temporal properties of the recorded audio snippet.

FIG. 1 shows an example of a time frame i shown in dotted lines and a preceding time frame i−1 overlapping therewith shown in broken lines.

Onset detection confirmation may be done by analyzing one pair or more pairs of consecutive time frames. Onset detection uses the frequency domain and may include a step of determining respective differences of the logarithms (log 2(.)) of the magnitudes of the Fast Fourier Transforms (FFTs) of these two consecutive time frames. A Discrete Fourier Transform may also be used for that purpose, as the invention is not limited in this regard.

A specific spectral frequency range of interest may then be selected, such as by dividing the frequency range of the time frames of the audio snippet into a plurality of bins, wherein each bin corresponds to a single frequency or predefined narrow range of acoustic frequencies. The number of bins and their corresponding frequencies may be selected based on the quality of the recorded audio snippet. In general, the better the quality of the audio snippet, the higher the frequency range of that audio snippet. This allows for the designation of more bins, which leads to a higher confidence in the outcome of the analysis. For example, a telephone line audio quality may have a limited bandwidth of about 8,000 Hz. In this case, 128 evenly spaced apart (on the frequency scale) bins may be used. This provides a "frequency resolution" of 8,000/128=62.5 Hz. In other words, each bin is separated from adjacent bins by 62.5 Hz. In other embodiments, a higher number of bins may be used to improve "frequency resolution." In the same example of a telephone line audio recording, using 2048 bins leads to a smaller frequency difference between adjacent bins of only 3.9 Hz.

In embodiments, any number of bins above about 50 bins may be used. A higher number of bins improves the outcome confidence but requires a higher computation power. Selecting the number of bins as a power of two may be used to speed up these calculations, such as selecting a total of 128 bins, 256 bins, 512 bins, 1024 bins, or 2048 bins.

The selected plurality of bins may be numbered as bin number $K_{min}$ up to a bin number $K_{max}$. A comparison then may be made of each bin's magnitude of the current frame i to the corresponding bin's magnitude of the previous frame i−1. This comparison may be performed via subtraction. For each designated frequency bin, if the magnitude difference exceeds a predefined acoustic energy limit $T_1$, this bin is assigned a value of one. Otherwise, this frequency bin is assigned a value of zero—see FIGS. 2 and 3.

Figure 2:
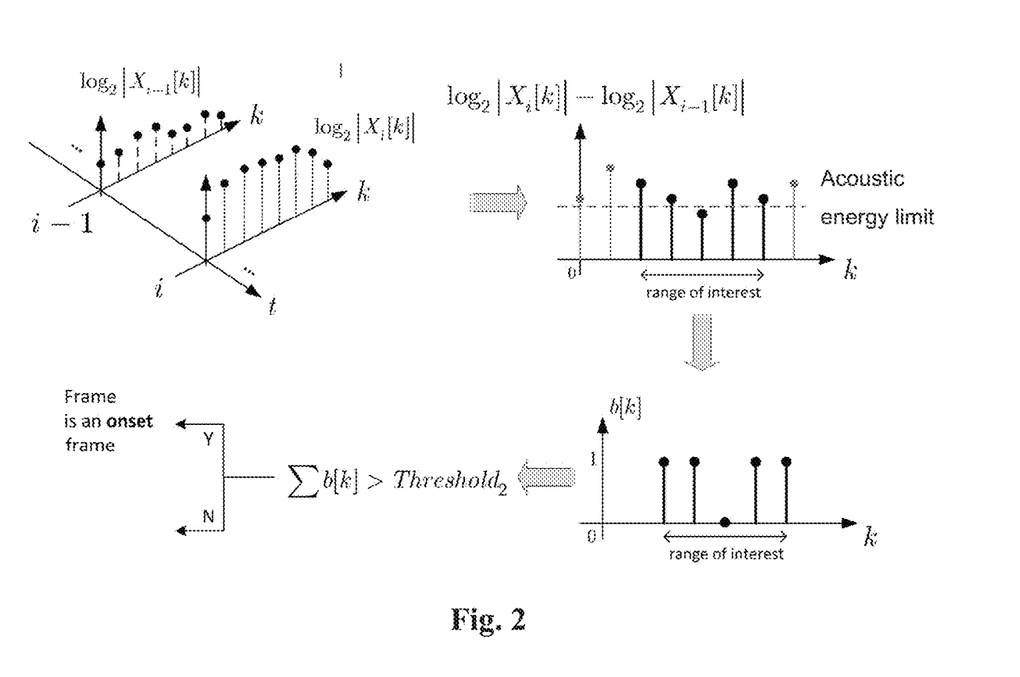
FIG. 2 is a diagram illustrating determination of an onset of a cough event according to the method of the invention.
Figure 3:
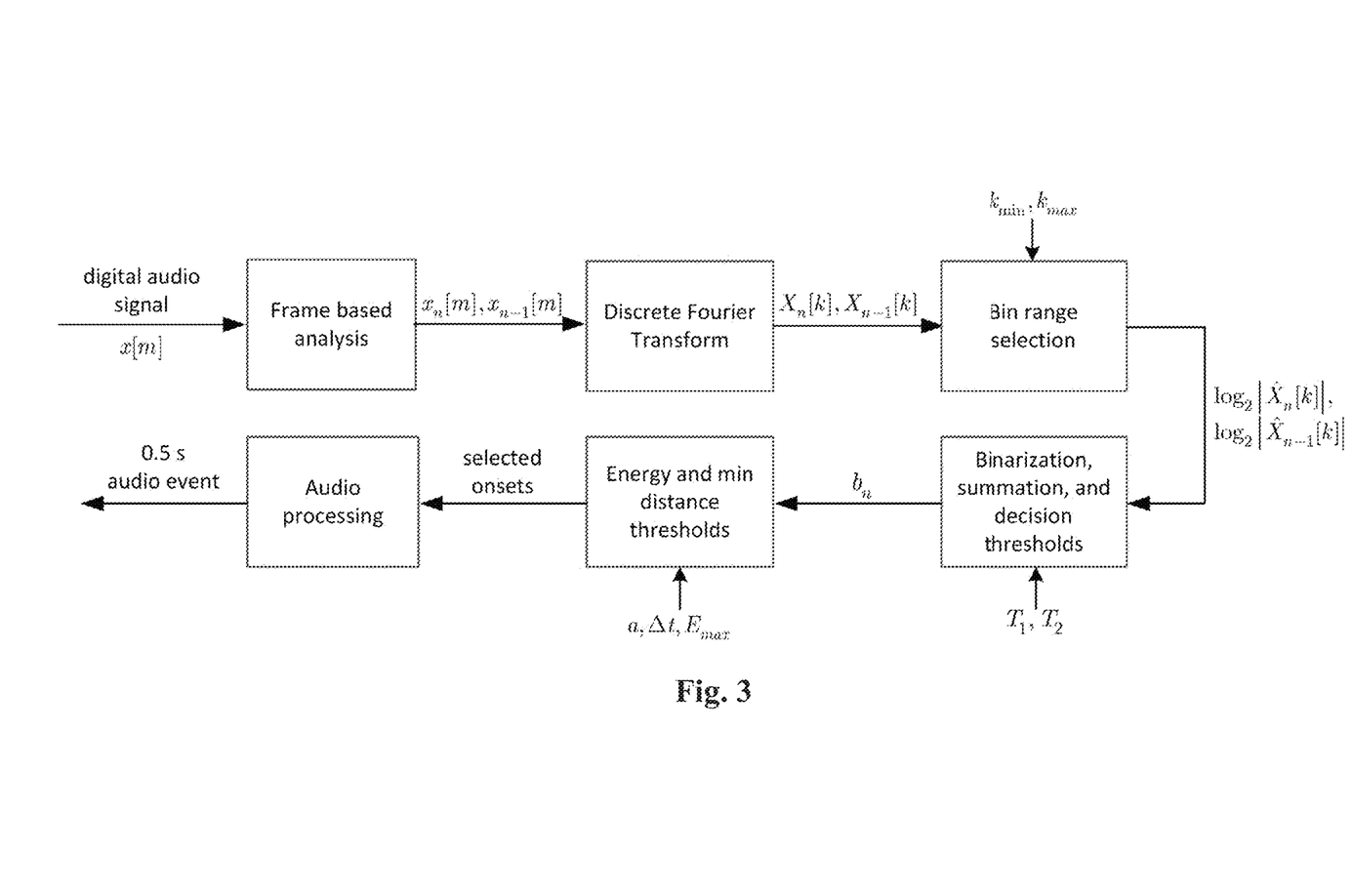
FIG. 3 is a block diagram of steps, including data processing of the audio signal recordings.

If the sum of all binary values in the selected frequency range exceeds a second predefined threshold $T_2$, then this means that there is a significant acoustic energy change between the two selected consecutive frames, i and i−1, leading to the current frame i being declared as an onset frame of a possible cough event. Finally, a time-domain energy threshold is additionally considered. Let $E_n$ denote the $L_1$ norm of each frame in the frequency domain range of interest: a frame is not considered to be an onset frame if its $L_1$ norm is greater than a times the highest of all $L_1$ norms of frames in the recording. Variable a is a fixed number less between 0.05 and 0.5. Finally, since two or more successive frames can be labeled as onset frames, a minimum amount of time Δt between successive onsets is assumed.

Figure 4:
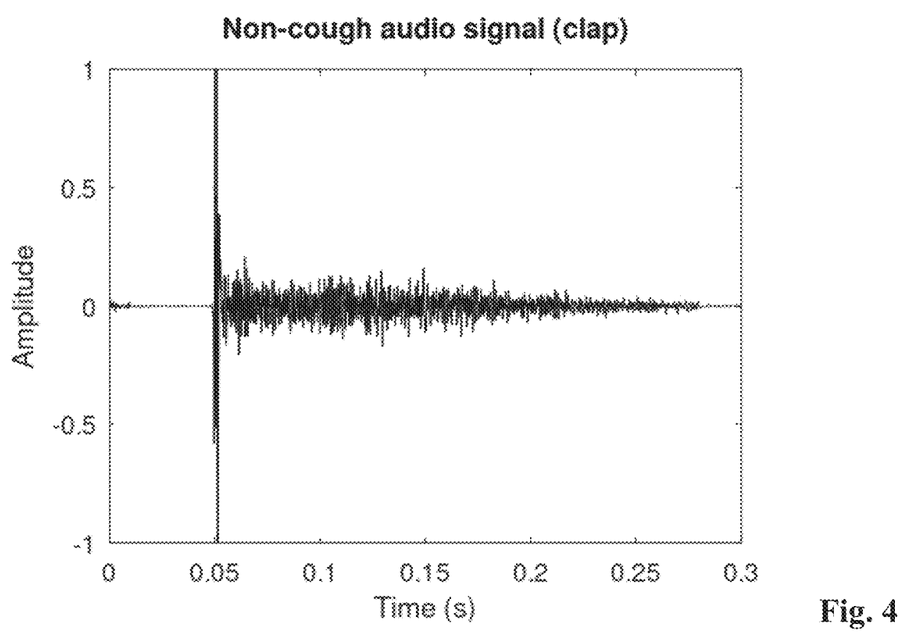
FIG. 4 is an exemplary temporal plot of audio signal amplitude for a known non-cough event.
Figure 5:
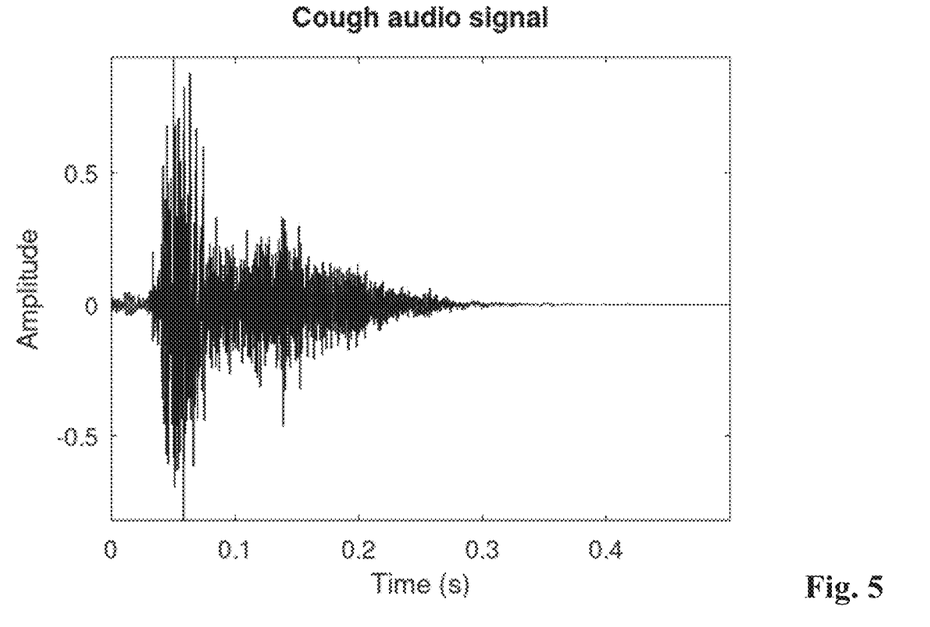
FIG. 5 is an exemplary temporal plot of audio signal amplitude for a known cough event.

As mentioned above, not all abrupt and loud sounds are cough events. FIG. 4 shows a typical example of a non-cough event (clap), while FIG. 5 shows a typical example of a true cough event. At first blush, these events look similar to each other. The remaining portion of the method describes steps aimed at differentiating cough events from non-cough events.

According to the present invention, a step of classifying the previously recorded audio snippet as cough or non-cough comprises a step of using a statistical classifier. A number of statistical classifiers may be used for this step of the invention, such as the following non-limiting list of statistical classifiers:

Convolutional neural network
Recurrent neural network
Logistic regression
Naive Bayes classifier
Support Vector Machines
Random Forest
Decision Tree
Multilayer Perceptron
Support Vector Machine
K Nearest Neighbors The present invention is described in connection with a convolutional neural network classifier. A convolutional neural network is a specialized type of neural network used primarily for processing data with a grid-like topology, such as images. It consists of one or more convolutional layers, often followed by pooling layers, dropout layers, and batch normalization layers. The key feature of a convolutional neural network is the convolutional layer, where small regions of the input are processed through filters (or kernels). These filters slide across the input to produce feature maps, capturing local dependencies and reducing the spatial size of the representation, which makes the network more efficient and reduces the number of parameters. Pooling layers, typically following the convolutional layers, further downsample the spatial dimensions of the representation, providing translation invariance and compressing information. After several convolutional and pooling layers, the high-level reasoning in the network is done via fully connected layers, where neurons are connected to all activations in the previous layer. Generally speaking, convolutional neural networks are widely used in image and video recognition, image classification, medical image analysis, and many other areas where pattern recognition from visual inputs is essential. They are effective because they exploit the spatially-local correlation present in images through the application of relevant filters, reducing the number of parameters required compared to fully connected networks, and thus reducing the computational burden.

Figure 6:
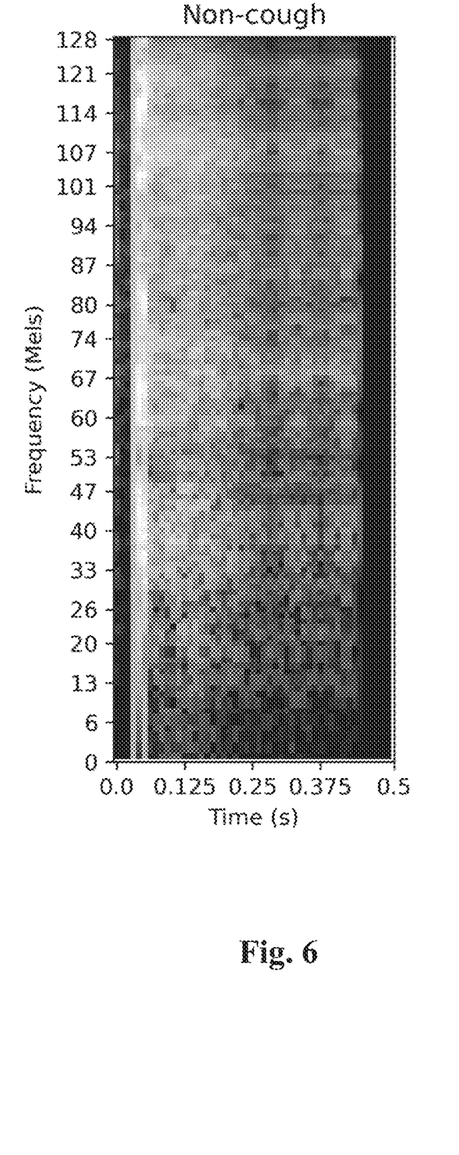
FIG. 6 is an exemplary image of a known non-cough event in the frequency-time domain.
Figure 7:
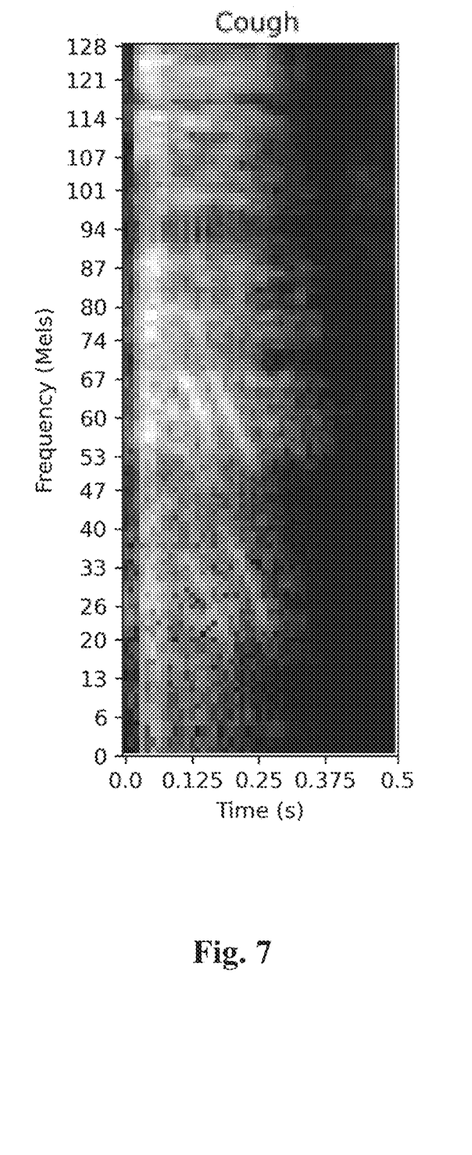
FIG. 7 is an exemplary image of a known cough event in the frequency-time domain.

The convolutional neural network may be configured for the purposes of the present invention by being pre-trained on a plurality of prior recordings of known human cough and non-cough events. Such prior recordings (for example, as seen in FIGS. 4 and 5) may be first processed by analyzing the acoustic energy distributions of each recording in the frequency-time domain. The extent of darkness of each pixel or dot of the time-frequency domain plot may represent the magnitude extent at that particular time-frequency point. FIG. 6 is an example of such a frequency-time image for a known non-cough event. FIG. 7 is the same but for a known cough event.

Figure 8:
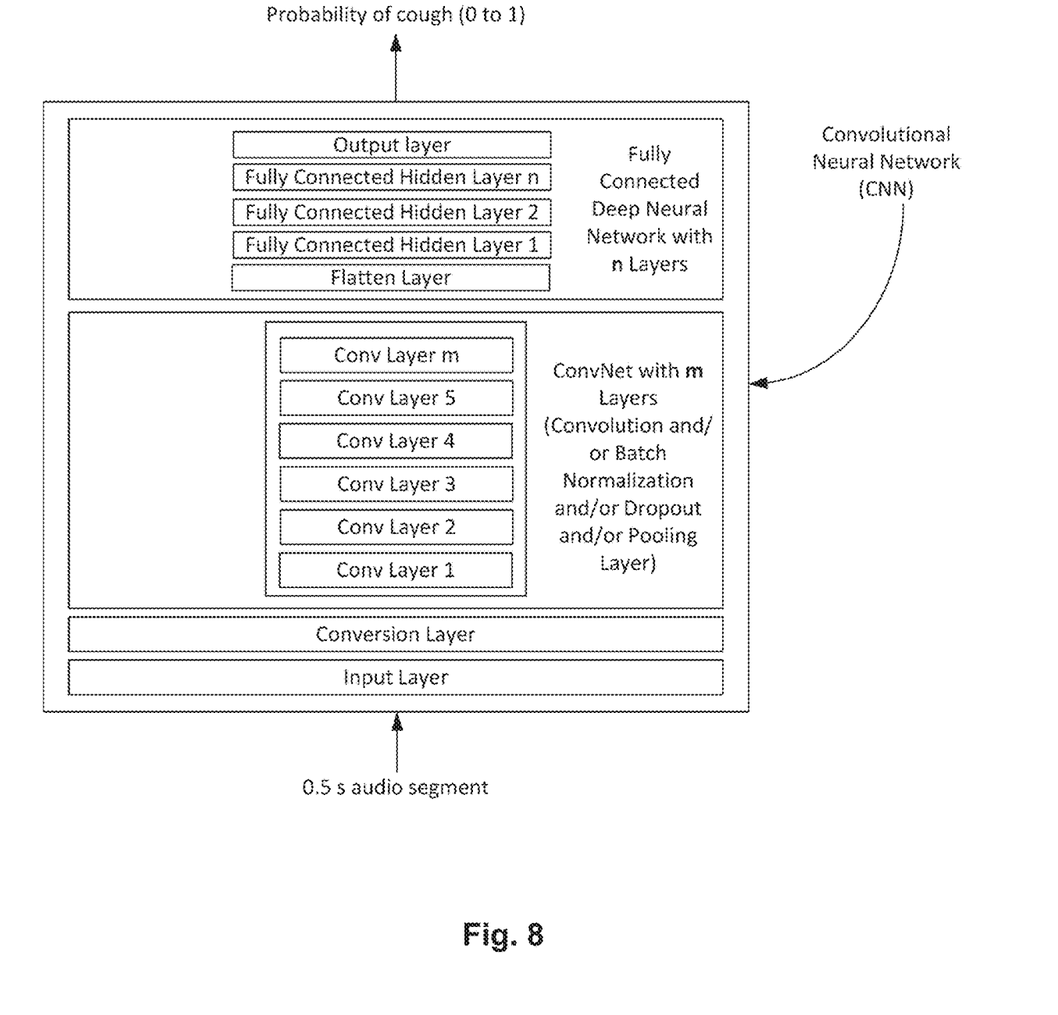
FIG. 8 is a block-diagram illustrating using a convolutional neural network for classifying audio snippets as cough or non-cough events.

More specifically, as illustrated in FIG. 8, the convolutional neural network of the invention may consist of a ConvNet comprising m l layers named Conv Layers, where m may be between 2 and 6, followed by a Fully Connected Deep Neural Network comprising n fully connected hidden layers, where n may be between 1 and 4. Each Conv Layer of the ConvNet may consist of a convolution layer, a batch normalization layer, a dropout layer, and a pooling layer. In some embodiments, the batch normalization layer may be omitted.

Each convolution layer may be equipped with a set of 2D kernels that are usually 3×3, 4×4, 5×5, etc. that "scan" the 2D-spectrotemporal representation images of the pre-recorded samples in a sequential manner (meaning top line first, then move to the next line, and so on), with the difference that it reads in "3×3 or 5×5 square blocks" and not in 1×1 blocks as done in conventional reading. The process is adapted to learn some of the very basic features of each representation image, for example, high energy regions, sharp vertical transitions, etc. Deeper layers learn more specific patterns and features of the representation image.

The batch normalization layer may be used to regularize the output of the convolution layer in order to make learning more efficient. The pooling layer may also be a sampling layer it takes the output of the previous layer and downsizes it to keep only the important information (by taking the maximum value in each "neighborhood" of the image). The dropout layer is a regularization layer where a random subset of neurons is temporarily excluded during each training iteration, helping prevent overfitting and promoting better generalization.

The same may be repeated when advanced on to the next Conv Layer. In general, earlier Conv Layers learn general features of the input image, while later Conv Layers learn more specific features.

The convolutional neural network of the present invention may comprise some additional layers. Examples of such additional layers include as follows:

a) a conversion layer, which may be used to transform the audio snippet to a 2D-spectrotemporal image representation, if that was not done before somewhere else.
b) a flatten layer, which may be configured to transform a M×N×D tensor to a 1×(M×N×D) vector. This layer turns the 2D representations into a 1D representation. This may be required for further processing by the fully connected hidden layers.
c) a series of n fully connected hidden layers, receiving a flattened vector of features from the ConvNet. Each neuron in subsequent layers is connected to every neuron in the previous layer via weighted connections. The input vector undergoes a linear transformation, where each element is multiplied by its corresponding weight, and the results are summed for each neuron in the layer, with biases added. This weighted sum is then passed through a non-linear activation function, introducing the crucial element of non-linearity. The activation function may be a sigmoid, a rectified linear unit (ReLU), a hyperbolic tangent (tanh), or any other non-linear continuous differentiable function. This process, including the linear transformation and activation, is repeated through multiple hidden layers, culminating in the output layer. The final output layer produces the network's predictions. This fully connected architecture allows the network to learn complex relationships within the features obtained from the ConvNet. Fully connected hidden layers may also include a dropout layer between two successive hidden layers.
d) an output layer a layer with a single output that is the probability measure of the audio snippet being a cough. In embodiments, that probability measure may be a number between zero and one. In other embodiments, the output layer may have two outputs, such as a probability measure for the cough class and a probability measure for the non-cough class. Of course, their sum is equal to 1.

One of the novel features of the present invention is a step of converting audio signals to images seen in FIGS. 6 and 7, which allows using convolutional neural networks to discern between cough and non-cough events. These images are acoustic energy, time-frequency-domain representations of an audio signal. These representations can be spectrograms, mel-spectrograms, mel-frequency cepstral coefficients or other similar representations. The mel-spectrogram is a powerful representation that combines the benefits of both traditional spectrograms and the mel-scale, providing a more perceptually relevant frequency scale for human auditory perception.

The mel-scale is a perceptual scale of pitches that approximates the human ear's response to different frequencies. This scale is non-linear and reflects the way humans perceive differences in pitch. Incorporating the mel-scale into the spectrogram allows for a more accurate representation of the frequency content of an audio signal as perceived by the human auditory system. The spectrogram, on the other hand, provides a visual representation of the spectrum of frequencies in an audio signal over time. It breaks down the signal into its constituent frequencies, with time on the horizontal axis and frequency on the vertical axis, revealing the temporal evolution of the signal's frequency components along with their energy evolution over time.

The mel-spectrogram is created by transforming the traditional spectrogram using a mel filterbank, which essentially converts the linear frequency scale into the mel-scale. This conversion involves passing the spectrogram through a series of overlapping triangular filters spaced according to the mel-scale. The resulting mel-spectrogram not only captures the time-frequency characteristics of the audio signal but also aligns more closely with the way humans perceive pitch. This method has been proven particularly valuable in applications such as speech recognition, where understanding the perceptual relevance of different frequency components is crucial.

In some embodiments of this system, the mel-spectrogram is generated using 40, 60, 96, or 128 filterbanks. The time frame can be 0.02, 0.04, or 0.05 seconds long, and the frame shift can be 0.01, 0.02, or 0.05 seconds long. For the frequency axis, the number of FFT bins can vary between 256 and 2048, depending on the bandwidth of the audio signal.

After the convolutional neural network is pre-trained on a plurality of similar images with known origin (cough or non-cough), this approach allows the computerized control unit to determine the probability measure of the future possible cough event to be a cough event or a non-cough event.

In addition to the times of true coughs, the system also detects and quantifies "cough-seconds." Cough-seconds are useful because (i) they correlate linearly with coughs and (ii) they provide a useful proxy for the amount of time spent coughing in the case of many sequential coughs in a bout. The computerized control unit may define the beginning of a cough-second as any confirmed explosive cough-classified onset that does not already form part of a prior cough-second. A cough second lasts exactly one second and contains all cough explosive phases that occur in the second after its initiation.

Uses of the Method of the Invention

The methods of the present invention may have a wide range of practical applications, now described in greater detail.

Coughing, a common symptom experienced by many, exhibits a notable lack of consistency and predictability in its patterns, especially in cases of persistent cough. This variability is evident in several aspects. First, the frequency of coughing bouts can vary significantly among individuals. Some may experience frequent, short bursts of coughing throughout the day, while others might have less frequent but prolonged episodes. The intensity and loudness of the cough also differ; some coughs are mild and barely audible, while others are harsh and disruptive.

Additionally, the time of day can also influence cough patterns, with some individuals experiencing worsening symptoms at night or early in the morning, potentially due to changes in body position or air quality.

Trigger factors for coughing episodes are another area of inconsistency. Certain individuals might find their cough exacerbated by environmental factors like pollen, pollution, or changes in weather, whereas others might have coughs that are more responsive to physical activities or even emotional states like stress or laughter.

The duration of a persistent cough also varies widely. While some people might experience a cough that resolves within a few weeks, others may endure symptoms for much longer, without a clear progression or pattern. This unpredictability can complicate diagnosis and treatment, as healthcare providers must consider a wide range of potential causes and contributing factors, from common conditions like asthma and gastroesophageal reflux to more serious issues like chronic obstructive pulmonary disease (COPD) or lung cancer.

Moreover, the response to treatments is equally varied among individuals with a persistent cough. While some might find relief with over-the-counter medications or inhalers, others may require more specialized treatments or may not respond to conventional therapies at all.

Finally, cough patterns are stochastic (good days and bad), so short-term measurements do not necessarily reflect longer-term trends.

The inventors of the present invention have surprisingly discovered that cough follows a negative binomial distribution. Generally speaking, a negative binomial distribution is a probability distribution that models the number of trials needed to achieve a specified number of successes in a sequence of independent and identically distributed Bernoulli trials. A Bernoulli trial is an experiment that results in a binary outcome: success or failure. The negative binomial distribution is found to be unexpectedly useful in analyzing cough patterns. This may be done by detecting successive cough bouts for a certain number of times until a determination is made that the series of cough bouts is statistically different from the previous records, therefore signifying an occurrence of a change in the cough pattern. Using the method of the invention allows this change to be detected with a variable, and often lower number of trials, as compared to a traditional analysis relying on a fixed number of trials as in conventional binomial distribution.

Understanding and recognizing this phenomenon, the inventors of the present invention have developed statistically rigorous ways to prospectively detect when the cough is out of normal for an individual. In addition, the use of the methods of the invention facilitates a retrospective analysis of the cough patterns for detecting a change point for an individual. This detection may be beneficial in conducting therapeutic trials or generally monitoring the efficacy of treatments designed to resolve the cough symptom of various diseases.

In addition, the use of the methods described above may be instrumental in diagnosing a condition and differentiating between different plausible conditions having cough as a common symptom. One example of such condition in postprandial cough associated with GERD. Coughing associated with Gastroesophageal Reflux Disease (GERD) typically presents as a long-lasting, chronic cough. Unlike coughs resulting from a cold, it is generally dry and not accompanied by phlegm. Patients with GERD often notice an exacerbation of coughing after eating, particularly following large meals or specific foods that trigger reflux. Coughing tends to worsen at night, likely due to the position facilitating the backflow of acid into the esophagus and throat. This type of cough can also be triggered or worsened by certain foods, alcohol, caffeine, and smoking, and might be resistant to treatments that usually alleviate other types of coughs.

Traditionally, diagnosing a cough due to GERD can be challenging and might require medical assessment and specific treatments to manage both the reflux and the cough. Understanding the fine details of the cough timing, frequency, and duration using the methods of the present invention may allow a more accurate diagnosis and follow-up monitoring of this condition.

The present invention may also find use in managing various chronic diseases, such as identifying exacerbation of COPD. In another example, understanding the timing of cough onset may be useful in identifying and avoiding persistent cough triggers, for example, large meals, pollution, humidity, or exercise.

Progression and efficacy of treatment may also be evaluated by changing or diminishing cough patterns that are objectively identified using the methods of the present invention.

Disease treatment may also be improved by providing real-time or near-real-time biofeedback to an individual to teach proper behavior or taking instant measures that avoid or at least diminish the onset of cough bouts.

Expanding the use of the invention methods from a single individual to monitoring groups of individuals may be useful in the early detection of airborne exposures of individuals to a pollutant or a bioweapon that may cause an onset of coughing. Finally, the methods of the invention may be useful in monitoring the overall health of a large group of individuals placed in the same location. An increase in cough for a normal group of people above historical levels may indicate an extent of prevalence of latent respiratory conditional or other anomalies or diseases, as well as the presence of an airborne pathogen or pollutant.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of automatically detecting cough events comprising the following steps:
   a. continuously recording ambient sound,
   b. upon detecting a change in ambient sound exceeding a predefined first threshold, identifying an onset of a possible cough event,
   c. recording an audio snippet including the onset of a possible cough event and continuing for a predefined audio snippet duration exceeding 100 msec thereafter,
   d. classifying the audio snippet recorded in step (c) as cough or non-cough based on analyzing acoustic energy distribution of the audio snippet in a frequency-time domain at a frequency above 100 Hz, e. discarding all identified non-cough events, f. repeating steps (b) through (e) if further possible cough events are identified after the audio snippet recorded in step (c), and g. compiling a record of all cough events detected during the recording of ambient sound in step (a).

2. The method of automatically detecting cough events, as in claim 1, wherein in step (g) the record of all cough events comprises none or at least one time stamp associated with the cough event classified in step (d).

3. The method of automatically detecting cough events, as in claim 1, wherein in step (d) classifying the audio snippet recorded in step (c) as cough or non-cough further comprises a step of comparing the acoustic energy distribution of the audio snippet against a predefined second threshold.

4. The method of automatically detecting cough events, as in claim 1, wherein in step (d) classifying the audio snippet recorded in step (c) as cough or non-cough comprises a step of using a statistical classifier.

5. The method of automatically detecting cough events, as in claim 4, wherein the statistical classifier is a neural network classifier.

6. The method of automatically detecting cough events, as in claim 5, wherein the neural network classifier is a convolutional neural network classifier.

7. The method of automatically detecting cough events, as in claim 6, wherein the convolutional neural network is pre-trained on a plurality of prior recordings of known human cough and non-cough events.

8. The method of automatically detecting cough events, as in claim 7, wherein the plurality of prior recordings of known human cough and non-cough events are processed to define a probability measure of the event to be a cough event or a non-cough event.

9. The method of automatically detecting cough events, as in claim 8, wherein the plurality of prior recordings of known human cough and non-cough events are processed by analyzing acoustic energy distributions of each recording in the frequency-time domain.

10. The method of automatically detecting cough events, as in claim 1, wherein in step (c) the predefined audio snippet duration does not exceed 1 sec after the onset of the possible cough event.

11. The method of automatically detecting cough events, as in claim 1, wherein in step (c) recording the audio snippet starts prior to the onset of the possible cough event.

12. The method of automatically detecting cough events, as in claim 11, wherein in step (c) recording the audio snippet starts at least 20 msec prior to the onset of the possible cough event.

13. The method of automatically detecting cough events, as in claim 1, wherein in step (b) detecting a change in acoustic energy comprises a step of detecting individual changes in acoustic energy in a plurality of bins, wherein each bin corresponds to a predefined range of acoustic frequencies.

14. The method of automatically detecting cough events, as in claim 13, wherein a predefined second threshold corresponds to a number of bins from the plurality of bins in which a detected change in acoustic energy exceeds a predefined acoustic energy limit.

15. The method of automatically detecting cough events, as in claim 1, wherein step (a) further comprises a step of removing silence sounds identified using a predefined silence threshold.

16. The method of automatically detecting cough events, as in claim 1, wherein in step (d), a step of analyzing the audio snippet comprises a step of dividing the audio snippet into a plurality of time frames.

17. The method of automatically detecting cough events, as in claim 16, wherein in step (d), all of the time frames of the plurality of time frames overlap with adjacent time frames.

\* \* \* \* \*